United States Patent
Le et al.

(10) Patent No.: US 9,945,814 B2
(45) Date of Patent: Apr. 17, 2018

(54) TOTAL INTEGRATED TUBE ANALYSIS

(71) Applicant: WESTINGHOUSE ELECTRIC COMPANY, LLC., Cranberry Township, PA (US)

(72) Inventors: Qui V. Le, Pittsburgh, PA (US); Stephen J. Beehner, Jeannette, PA (US)

(73) Assignee: Westinghouse Electric Company LLC, Cranberry Township, PA (US)

(*) Notice: Subject to any disclaimer, the term of this patent is extended or adjusted under 35 U.S.C. 154(b) by 319 days.

(21) Appl. No.: 14/800,076

(22) Filed: Jul. 15, 2015

(65) Prior Publication Data

US 2016/0018362 A1    Jan. 21, 2016

Related U.S. Application Data

(60) Provisional application No. 62/026,316, filed on Jul. 18, 2014.

(51) Int. Cl.
| | |
|---|---|
| *G01B 3/44* | (2006.01) |
| *G01B 3/52* | (2006.01) |
| *G01N 27/90* | (2006.01) |
| *F22B 1/02* | (2006.01) |
| *B24B 49/10* | (2006.01) |
| *F22B 35/00* | (2006.01) |

(52) U.S. Cl.
CPC ....... *G01N 27/9046* (2013.01); *B24B 49/105* (2013.01); *F22B 1/023* (2013.01); *F22B 35/004* (2013.01); *G01N 27/9073* (2013.01)

(58) Field of Classification Search
CPC ............ G01N 27/9046; G01N 27/9073; F22B 1/023; F22B 35/004; B24B 49/105
See application file for complete search history.

(56) References Cited

U.S. PATENT DOCUMENTS

| | | | |
|---|---|---|---|
| 6,519,535 B1 * | 2/2003 | Petri | ............... B21C 51/00 702/38 |
| 8,387,444 B2 | 3/2013 | Le | |
| 2003/0195710 A1 | 10/2003 | Junker et al. | |
| 2010/0185576 A1 | 7/2010 | Strizzi | |
| 2011/0172980 A1 | 7/2011 | Le | |

(Continued)

FOREIGN PATENT DOCUMENTS

| | | |
|---|---|---|
| JP | 2002-005898 A | 1/2002 |
| JP | 2007-183231 A | 7/2007 |

OTHER PUBLICATIONS

International Searching Authority, International Search Report and the Written Opinion for International Application No. PCT/US2015/040718, dated Sep. 24, 2015.

(Continued)

*Primary Examiner* — Toan Le
(74) *Attorney, Agent, or Firm* — Joseph C. Spadacene; Westinghouse Electric Company LLC

(57) ABSTRACT

The invention relates to improved systems and methods for inspecting the tubes of a steam generator of a nuclear reactor that involves modeling the steam generator, comparing signals of a tube from an eddy current sensor with aspects of the model to determine whether further analysis is required, employing primary and secondary analysis processes, and producing a combined report of the primary and secondary analysis results.

11 Claims, 5 Drawing Sheets

(56) References Cited

U.S. PATENT DOCUMENTS

2013/0085684 A1    4/2013  Le et al.
2013/0118420 A1*   5/2013  Toyoda .................... B21C 9/00
                                                    122/235.14
2014/0097834 A1    4/2014  Le et al.

OTHER PUBLICATIONS

Obrutsky, L. et al., "Steam Generator Inspections: Faster, Cheaper and Better, Are We There Yet?" IV Conferencia Panamericana de END, Buenos Aires—Oct. 2007, pp. 1-17.
Extended European search report, Application No./Patent No. 15821763.8-1020/3170184 PCT/US2015040718, 7 pages.

* cited by examiner

TOTAL INTEGRATED TUBE ANALYSIS

CROSS REFERENCE TO RELATED APPLICATION

This application claims priority under 35 U.S.C. § 119(e) to U.S. Provisional Patent Application Ser. No. 62/026,316, filed Jul. 18, 2014, entitled TOTAL INTEGRATED TUBE ANALYSIS, the content of which is incorporated herein by reference.

BACKGROUND

1. Field

This invention pertains in general to nuclear power plants and, more particularly, to systems and methods for evaluating the tubes of a steam generator of a nuclear power plant. In particular, the software tools and methods of the invention integrate two automated analysis processes and the results generated therefrom.

2. Description of Related Art

Nuclear power plants can be generally described as including a reactor that has one or more fuel cells, a primary loop that cools the reactor, and a secondary loop that drives a steam turbine to operate an electrical generator. Typically, such nuclear power plants additionally include a heat exchanger positioned between the primary and secondary loops. The heat exchanger is in the form of a steam generator which includes tubes that carry the primary coolant and a plenum that carries the secondary coolant in heat-exchange relationship with the tubes and therefore, with the primary coolant.

It is known in the industry that the tubes of a steam generator are subject to wear from mechanical vibration, corrosion, and other mechanisms. Both manual and automated processes have been developed to detect and address this concern. Period inspection of the tubes of a steam generator for wear is necessary to avoid failure of a tube and the consequences resulting therefrom, for example, potential nuclear contamination of the secondary loop.

Known manual and automated processes have limitations associated therewith. For example, methods of measuring tube-to-tube proximity (i.e., the spatial relationship between two adjacent steam generator tubes), a potential precursor for tube-to-tube contact wear, has been found to be cumbersome and unreliable. Guidelines, analysis training and process changes have been implemented in the art with varying levels of success.

A known method of inspecting the tubes of a steam generator involves the insertion of an eddy current sensor into one or more of the tubes. A signal is received from the eddy current sensor, which is in the form of a voltage and a phase angle. An analyst can review the signal data to ascertain the current condition of the tubes of the steam generator. However, the analyst must possess a high degree of expertise in order to accurately ascertain from the signal data the current condition of the tubes of the steam generator. A typical steam generator may possess between three thousand and twelve thousand tubes, by way of example, with each tube being several hundred inches in length. Thus, the review of eddy current data can require a large expenditure of time by the analyst.

Among the difficulties involved in the analysis of eddy current data is the determination of whether a signal is indicative of a possible failure of a portion of a tube or whether the signal is not indicative of such a failure. Each tube of a steam generator typically has a number of bends and mechanical supports. In passing an eddy current sensor through such a tube, the signal from the eddy current sensor will vary with each mechanical support and bend, and the signal also will vary in the presence of a flaw, such as a crack or a dent in the tube. As such, the difficulty in analysis involves the ability to determine whether a change in a signal from an eddy current is indicative of a known geometric aspect of a tube, such as a bend or support, in which case further analysis of the signal typically is unnecessary, or whether the change in signal from the eddy current sensor is indicative of a crack or a dent, in which case further analysis of the signal typically is necessary.

Current steam generator inspection processes, in accordance with industry guidelines, requires the operation of two separate and independent analysis processes. These processes, described as primary analysis and secondary analysis, are operated either manually or through an automated system. EPRI, an industry institute that issues guidelines, has established that, if both processes are being used, such processes have to be different, independent and qualified by EPRI. The output of each of the primary analysis and secondary analysis processes produces separate primary analysis and secondary analysis reports. These reports need to be resolved by a resolution process to produce a single final result, which eventually determines the overall conditions of the steam generator tubes.

Enhanced Automated Data Screening (EADS) and Real Time Automated Analysis (RTAA) are two automated analysis processes known in the art for use in inspecting steam generator tubes for degradation. EADS is a rule based vector extraction algorithm and RTAA is a noise based signal extraction algorithm. These algorithms complement each other and provide effective primary analysis and secondary analysis in compliance with current industry guidelines.

Both EADS and RTAA have proven records to be effective analysis methods for all type of steam generator inspection tubing. However, there are disadvantages associated with these known steam generator tube analysis processes. For example, significant time and effort may be necessary to analyzing the two separate reports and data generated by the EADS and RTAA analyses.

It is, therefore, an object of this invention to provide an automated analysis of steam generator tube conditions as an alternative to the existing inspection process. It is desired that two separate and independent automated analysis processes, e.g., a primary analysis and a secondary analysis, be combined and integrated into a single efficient automated analysis system. In addition, several supporting software modules may be integrated and run on a standard computer to produce final results accurately and promptly. The invention provides a combined analysis report from the two analysis processes to produce the final results of steam generator tubing inspection in a single report for review, enabling users to identify the automated analysis processes that generate the tube condition report entries, and integrating a noise evaluation process. This new automated analysis can demonstrate increased performance and reliability with respect to the evaluation of steam generator tubing data. It is anticipated that the results and the single report of the results will provide comprehensive steam generator repair solutions that will preclude failures and unplanned shutdowns that are time-consuming and costly.

SUMMARY

In one aspect, this invention provides a method of non-destructively assessing a current condition of a number of tubes of a steam generator of a nuclear power plant. The method includes:

(a) establishing a model of the steam generator that comprises a set of baseline parameters for each of a plurality of exemplary regions of interest (ROIs) of a number of the tubes of the steam generator;

(b) extracting a signal from each of a number of physical ROIs of a number of the tubes;

(c) comparing the signal from a given physical ROI of a tube with the set of baseline parameters of the corresponding exemplary ROI of the model;

(d) triggering additional processing when at least a portion of the signal from the given physical ROI exceeds at least a portion of the set of baseline parameters of the corresponding exemplary ROI; and (e) employing a primary analysis code for conducting steps (a) through (d);

(f) generating a first set of results based on the primary analysis code;

(g) employing a secondary analysis code for conducting steps (a) through (d);

(h) generating a second set of results based on the secondary analysis code;

(i) combining the first and second set of results; and (j) producing a single report including output from each of the first and second set of results, in the absence of duplicate entries.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1:
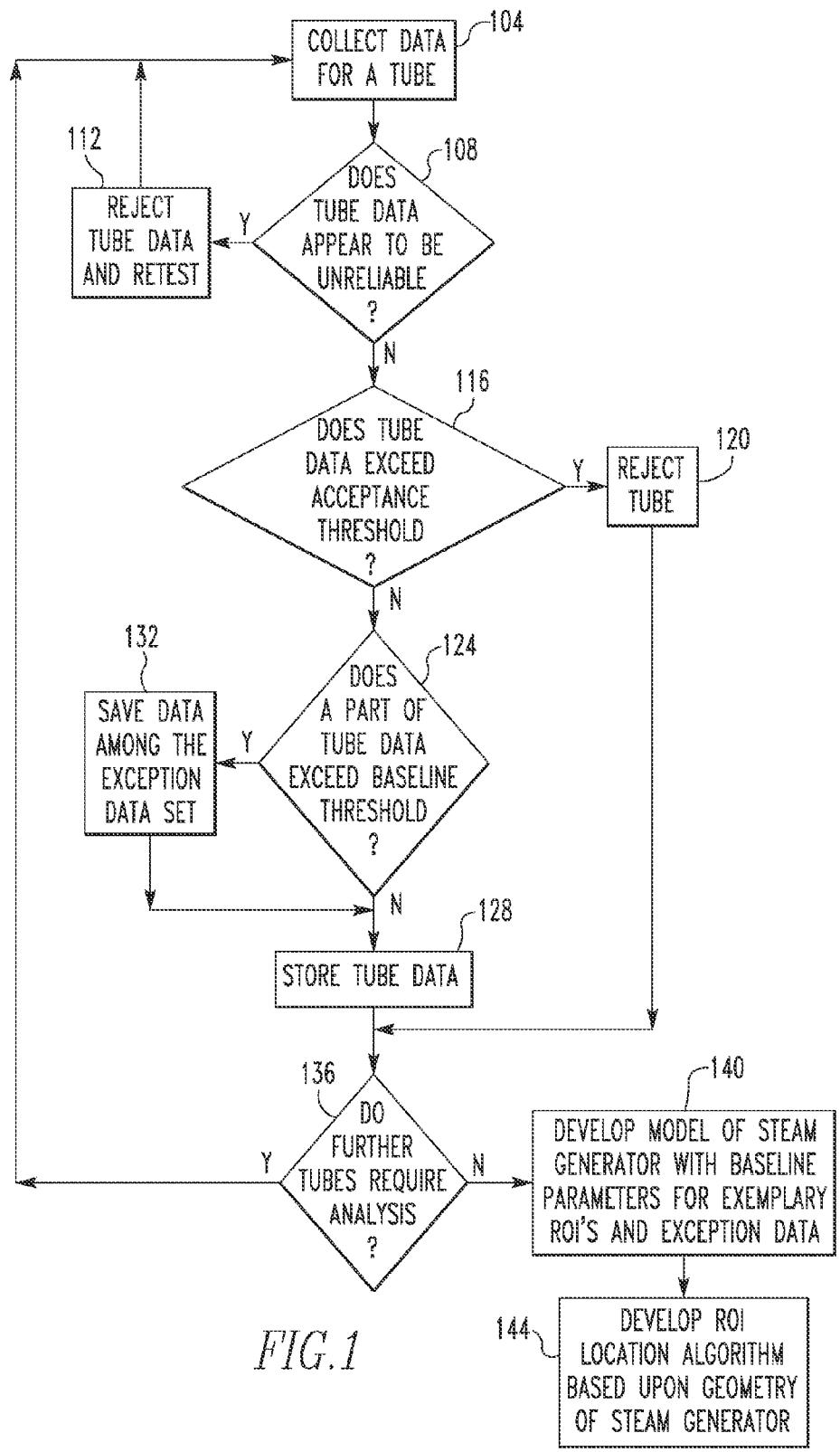
FIGS. 1 through 4 are each a flow chart depicting steps included in the method of the invention.

The invention relates to software tools and methods to inspect steam generator tubes, verify analysis coverage of areas of interest for the steam generator tube inspection and, to resolve and report the results provided therefrom. These software tools and methods are applicable to various steam generator designs and the processes employed for inspection of the tubes disposed therein. In certain embodiments of the invention, the steam generator is positioned within a nuclear reactor plant, such as a pressurized water reactor plant or a boiling water reactor plant. Steam generator tube inspections typically employ automated analysis processes which includes setup and, subsequently, analysis.

The tools and methods of the invention pertain to conducting steam generator inspections in accordance with EPRI Steam Generator Inspection Guidelines, which require utilizing two separate and independent analysis processes. The two processes are referred to as primary and secondary automated analysis processes. Accordingly, the invention includes combining the primary and secondary automated analysis processes to produce integrated steam generator eddy current data and a producing a single output report for ease of reviewing and resolving the data to detect tube wear and degradation.

Certain aspects of the methodologies employed herein involve the collection of data with the use of an eddy current sensor that is received within the interior of an elongated tube of a steam generator and that is passed through the interior of the tube along the longitudinal extend thereof. Longitudinal movement of the sensor can be performed manually, although it can also advantageously be performed by a robotically-controlled advancement mechanism that advances the eddy current sensor at a controlled rate and that is capable of providing a data stream component representative of the longitudinal distance of the eddy current sensor along the tube at any given time. Other data streams from the eddy current sensor typically include a voltage component that characterizes an amplitude and another component that characterizes a phase angle.

As above-described, current steam generator inspection processes per industry guidelines requires the operation of two separate and independent analysis processes. In accordance with certain embodiments of the invention, the first analysis process is Enhanced Automated Data Screening (EADS) and the second analysis process is Real Time Automated analysis (RTAA). The invention combines and integrates these two processes and, the data and report produced therefrom. In certain embodiments, the invention is known and referred to as Total Integrated Tube Analysis (TITAN).

The setup for each of the EADS and RTAA processes generally includes mapping the steam generator tubes to be inspected and the supporting structures. The configuration parameters for the tubes and structures are input into a setup portion of the software program. For example, the information entered into the setup can include the number of steam generator tubes, the length of the steam generator tubes, and the like. This information can be specific to particular steam generator designs and nuclear reactor plants. In certain embodiments, steam generator tubes can be mapped as follows. The length of each of the steam generator tubes is partitioned into a plurality of segments. The length of each segment is measured and recorded. In this embodiment, a landmark is established and the offset from the landmark is measured. The landmark represents one endpoint of the segment and the offset represents the distance or length to the other endpoint of the segment. This segmentation process can be carried out until a specified steam generator tube distance is covered. In certain embodiments, this process is carried out initiating with the steam generator tube end at the hot leg, extending through the u-bend and ending with the tube end at the cold leg. Thus, the landmark is located at the tube end of the hot leg and the offset therefrom is determined for each successive end point or segment. Alternatively, an end point for one segment can then serve as the landmark for another (consecutive) segment. Similar segments are grouped together to create a Region of Interest (ROI). Each ROI has its own characteristics and is subject to certain operating conditions. As a result, each ROI is often subjected to a different type of degradation. For example, a ROI of a U-bend area in the tube is often subject to wear due to higher frequency of vibration, whereas a ROI of a tube sheet may have cracks due to chemical reaction from sludge/deposit that interact with the tube.

As is generally understood, a typical steam generator includes a plenum that encloses perhaps four thousand to twelve thousand individual tubes that each comprise a hot leg and a cold leg that pass through a tube sheet, which is itself a slab of metal that is typically twenty or more inches thick. Each tube may be several hundred inches long and have either a single U-bend or a pair of elbow bends, although other geometries can be employed without departing from the present concept. Each such tube typically additionally includes twenty to thirty physical supports of differing geometries. During initial manufacture, the hot and cold legs of each tube are assembled to the tube sheet by receiving the two ends of the tube in a pair of holes drilled through the tube sheet and by hydraulically bulging the ends of the tube into engagement with the cylindrical walls of the drilled holes.

While the geometry of each tube of a steam generator typically is different from nearly every other tube of the steam generator, the overall construction of the steam generator enables generalizations to be made with regard to the geometry of the tubes as a whole. That is, each tube can be said to include a pair of tube sheet transitions at the ends thereof which typically are characterized by an eddy current sensor voltage on the order of thirty (30.0) volts. Between the two tube sheet transitions are various straight runs, supports, and bends. The typical eddy current voltage for a straight section of tube is 0.05 volts, and the typical voltage for a bend of a tube is 0.1 volts. A typical voltage for a support may be 0.2 volts, but various types of supports can exist within a given steam generator, all of which may produce different characteristic voltages.

Advantageously, however, the various arrangements of straight sections, supports, and bends as a function of distance along a tube are of a limited number of permutations within any given steam generator. As such, a location algorithm is advantageously developed from the known geometry of the steam generator and the historic data that can be collected from the steam generator, wherein an input to the algorithm of a series of voltage and distance values can identify a particular region of interest (ROI) of a tube that is under analysis. That is, the wear that is experienced by a tube often can occur at a tube sheet transition, at a location of attachment of a tube to a mechanical support, at a transition between a straight section and a bend in a tube, or at other well understood locations. The various segments of a given tube can be divided into various ROIs which can be identified during data collection with a high degree of accuracy based upon the details of the steam generator geometry that are incorporated into the location algorithm. As such, by inputting voltage, phase, and distance data into the location algorithm, the location algorithm can identify a specific segment and thus physical ROI of the tube being analyzed.

The invention can also be said to include the development of a model for the steam generator that includes baseline parameters such as voltage and phase for each of a plurality of exemplary ROIs that exist in the particular steam generator.

Advantageously, and as will be set forth in greater detail below, the model additionally includes exception data for particular ROIs of particular tubes that have voltage and/or phase angle parameters that would exceed the baseline parameters of the corresponding ROI of the model but that are nevertheless acceptable, i.e., the signals from such ROIs are not themselves indicative of flaws that require further evaluation by an analyst.

The baseline parameters for the various exemplary ROIs of the model can be established in any of a variety of ways. In the exemplary embodiment described herein, the various baseline parameters for the various exemplary ROIs of the model are established based upon theoretical evaluation of tubes and their ROIs, as well as experimental data based upon eddy current analysis of actual tubes and their physical ROIs. The direct physical analysis of tubes such as through the collection of eddy current data of individual tubes of a steam generator advantageously enables the collection of data with respect to typical ROIs that can be employed in establishing baseline parameters for exemplary ROIs of the model. Such direct physical analysis of tubes can additionally be employed to collect data that is later stored as exception data for particular ROIs of particular tubes.

Additionally and advantageously, such direct collection of eddy current data during the initial manufacture of a steam generator can enable an initial evaluation of each tube to assess whether the tube should be rejected or whether the data appears to be unreliable and should be recollected. A tube may be rejected if the data suggests that it is defective in manufacture. On the other hand, the data may need to be recollected if it appears that the eddy current sensor was functioning improperly or if other data collection aspects appear to be erroneous or unreliable.

The setup for the automated analysis process further includes the potential to selectively analyze the steam generator tubes for various abnormalities and degradation. This is referred to as the auto analysis sort. The mode of analysis can vary and include degradation detection, tube geometry variation and/or loose part detection. In certain embodiments, the auto analysis sort can include dents, dings, flaws and the like. The analysis process provides the capability to selectively inspect the steam generator tubes for only one abnormality or, alternatively, to inspect for a plurality of abnormalities.

The analysis coverage verification for EADS includes the following two parts: an automated Analysis Gap Tool (AGT) and an automated Report Extent Verification. The AGT provides a visual display of EADS coverage for a given steam generator model. Therefore, a visual verification of complete coverage and the absence or presence of gaps in coverage can be observed for each mode of the analysis. Thus, for example, AGT can show coverage for analysis of dents, dings and flaws for each segment of a steam generator tube. Further, AGT can show if a particular segment of the steam generator tube was not analyzed for one or more of dents, dings and flaws. EADS creates an automated report that contains the extent of the analysis and includes error messages to identify any analysis mode coverage problems, e.g., gaps in analysis. For example, the automated report can generate an error message to identify the particular segment of a steam generator tube that was not analyzed for one or more of dents, dings and flaws. The report is loaded into a database and analysis extent verification is performed to confirm that the extent of the analysis meets the extent of the planned inspection.

RTAA software is capable of performing a total signal and noise analysis. RTAA is an automated analysis process which is generally known in the art for use in inspecting steam generator tubes for degradation. A true measurement of the baseline signal can be accomplished using rolling noise window measurement. In certain embodiments, this concept and method are used to generate a baseline inspection of tube U-bends and tube supports and transitions to determine wear. In other embodiments, this concept and method is used to generate a baseline inspection of straight length tube sections to determine whether the tube is bent such that it may contact adjacent tubes.

RTAA performs additional verification in real time for each steam generator tube analyzed. The RTAA checks for each data point within the planned inspection to ensure that it has been measured by at least one method of noise measurement, such as free span noise measurement or a structure-related noise measurement. If there is a gap in noise measurements, which may be indicative of a gap in coverage, RTAA will abort and create an error message in the noise monitoring log. The noise measurement values are loaded into a database and a final check of all expected noise measurements is conducted. The database provides verification for each ROI that the number of noise measurements is within the expected tolerance and that the value of the noise measurements is also as expected. Extreme deviation from the number of measurements or the expected value of measurements will be flagged for disposition.

FIG. 1 generally depicts an exemplary methodology for the collection of tube data which enables the development of a model of a steam generator and the development of a location algorithm that is based upon the geometry of the steam generator. Processing begins, as at 104, where eddy current data is collected for a given tube of the steam generator. As mentioned herein, the data stream typically will include components of voltage, phase, and distance, all of which can be detected as a continuous signal or as a discrete set of data points along the length of the tube.

In FIG. 1, processing continues at 108, where it is determined whether the data derived from the eddy current sensor signal is potentially unreliable. For instance, if the data suggests a possible data collection error, processing continues as at 112, where the tube data is rejected, and the tube is retested. Processing thereafter would continue, as at 104. However, if at 108 the data is not determined to be unreliable, processing continues, as at 116, where it is determined whether the tube data derived from the eddy current signal exceeds an acceptance threshold, such as would indicate that the tube itself is mechanically or otherwise defective. In the event that the data exceeds an acceptance threshold, the tube is rejected, as at 120.

If the tube data does not exceed the acceptance threshold at 116, processing continues, as at 124, where it is determined whether any portions of the tube data exceed what should theoretically be the baseline parameters of that portion of the tube, i.e., the baseline parameters for the corresponding exemplary ROI of the model of the steam generator. By way of example, it may be determined that the physical ROI of the tube that is under analysis includes a physical support and the eddy current sensor is indicating a voltage of 0.4 volts. While an analyst may determine that the voltage that would typically be expected for such an ROI is 0.2 volts, the analyst may nevertheless determine that the particular physical ROI is acceptable and that the voltage of 0.4 volts is an acceptable anomaly. In such a circumstance, the data for the particular ROI for this particular tube will be saved, as at 132, as a portion of an exception data set. In this regard, it is reiterated that the tube or its data would already have been rejected, as at 112 or 120 respectively, if the data for the aforementioned ROI suggested that the ROI would be unacceptable.

Referring to FIG. 1, processing continues from both 124 and 132 onward to 128 where the tube data is stored in a data set. It is then determined, as at 136, whether further tubes require eddy current analysis as set forth above. If further tubes await testing, processing continues, as at 104, with a new tube. Otherwise, processing continues, as at 140, where the model of the steam generator is developed with a set of baseline parameters for each of a plurality of exemplary ROIs. The model further includes the aforementioned exception data for one or more particular ROIs of one or more particular tubes. It is understood that the inclusion as at 140 of the development of the steam generator model at this particular location within the exemplary methodology is intended to be merely an example of a point at which a model of the steam generator can be developed. It is understood that with analytical methods, at least an initial model of the steam generator can be developed, with the experimental collection of tube data from 104 through 132 being supplied to the model to provide refinement of the model and to provide exception data. It thus is understood that the model of the steam generator can be developed in whole or in part at any time depending upon the data and the analysis that are available.

Referring to FIG. 1, processing continues to 144 where the location algorithm which identifies various ROIs can be developed based upon the geometry of the steam generator and other factors. As was mentioned elsewhere herein with respect to the development of the model of the steam generator, the location algorithm can likewise be developed in whole or in part at any time depending upon the analytical and experimental data that is available in the development process depicted generally in FIG. 1. When completed, the location algorithm advantageously can receive a data stream from an eddy current sensor within the tube of the steam generator and can employ the voltage, phase, and distance data components to identify any of a variety of exemplary ROIs that are stored within the model of the steam generator. That is, the location algorithm can employ the eddy current signal within a tube of the steam generator to identify a particular segment of the tube and thus a physical ROI of the tube, and the location algorithm can additionally identify from the model that was developed of the steam generator a corresponding exemplary ROI and its baseline parameters for comparison with the eddy current signal that is being collected from the physical ROI.

Figure 2:
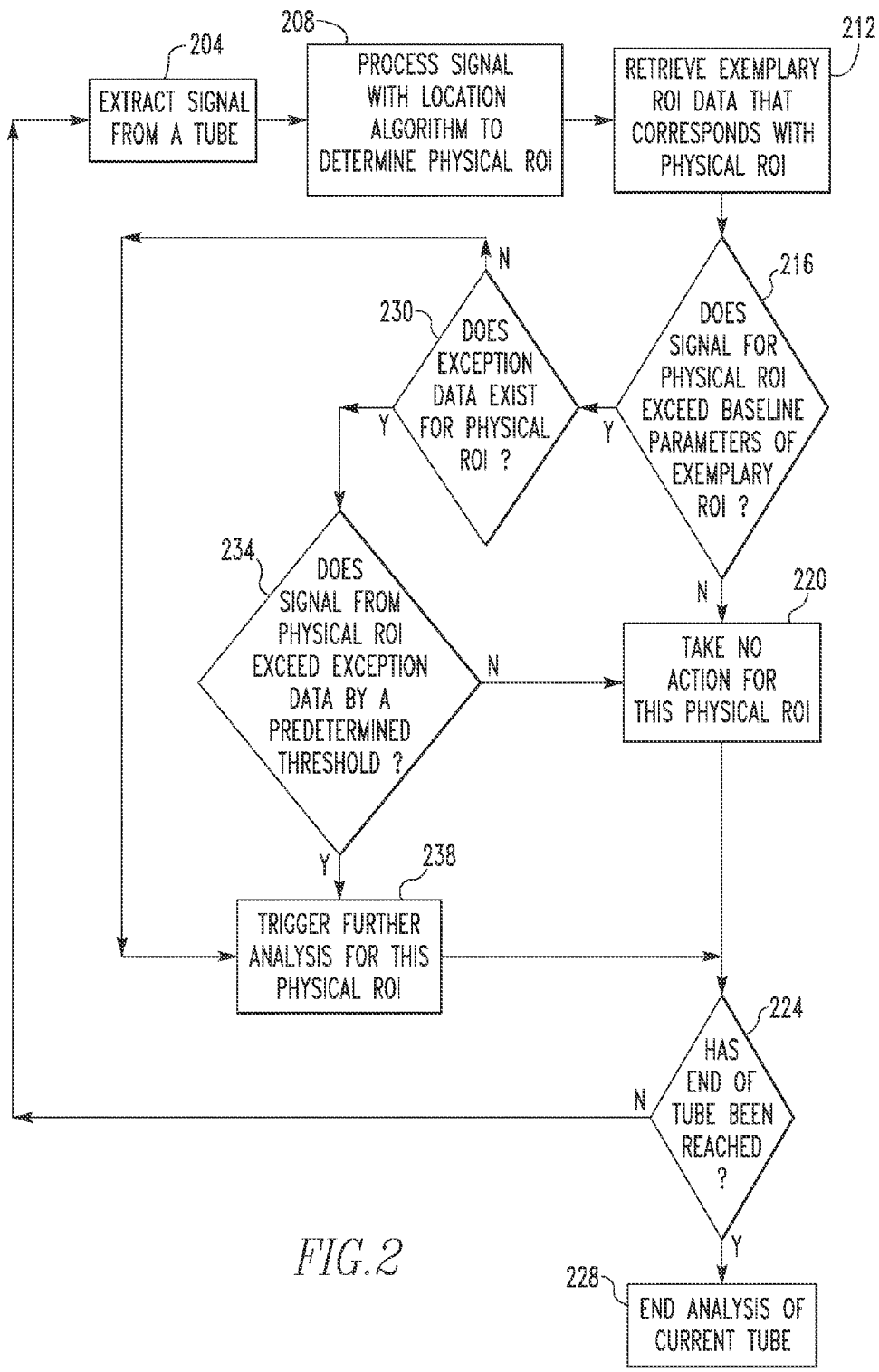

The testing of the tubes of a steam generator is depicted in an exemplary fashion in FIG. 2. It is understood that the operations depicted generally in FIG. 1 typically will occur at a first time and will be in the nature of a historic data set. The operations occurring in FIG. 2 typically occur at a second, subsequent time and may more likely be directed toward current or present testing of a steam generator. Processing begins, as at 204, where a signal is extracted from a tube of the steam generator. The signal from the eddy current sensor is processed with the aforementioned location algorithm, as at 208, to determine the physical ROI that is the source of the signal that is being collected from the tube under analysis. The location algorithm then employs, as at 212, the signal from the eddy current sensor to retrieve from the model an exemplary ROI that is determined to correspond with the physical ROI that has been located by the location algorithm. It is then determined, as at 216, whether the signal data for the physical ROI exceeds the baseline parameters of the exemplary ROI from the model that was identified and retrieved at 212. If it is determined at 216 that the eddy current signal for the physical ROI does not exceed the baseline parameters of the exemplary ROI, processing will continue, as at 220, where no further action will be taken with respect to this particular physical ROI. That is, no additional analysis will be triggered for this particular physical ROI, thereby avoiding the need for an analyst to perform any evaluation with respect to this physical ROI.

It is then determined, as at 224, whether the end of the tube under analysis has been reached. If so, the analysis of the current tube ends, as at 228. Another tube can then be analyzed. However, if the end of the tube is determined at 224 to not be reached, processing continues, as at 204, where the eddy current signal is continued to be extracted from the tube under analysis.

The aforementioned baseline parameters of the various exemplary ROIs of the model can be developed in any of a variety of fashions. Most typically, the baseline parameters will be developed with the use of theoretical data and experimental data, as suggested above. For instance, the typical eddy current voltage that one might expect to detect from a straight section of a tube is 0.05 volts, and the data collection effort depicted generally in FIG. 1 might demonstrate, by way of example, that the tested voltage values for each straight segment of each tube is 0.08 volts or less. As such, the baseline voltage for an exemplary ROI that corresponds with a straight section of a tube might be established 0.1 volts. This would enable all physical ROIs that are straight sections of tubes to, in their original condition, not exceed the baseline parameter of 0.1 volts and thus not trigger the need for further analysis, as at 220.

Similarly, the typical eddy current sensor voltage that one might expect from a curved section of a tube is 0.1 volts, and the baseline parameter for experimental ROIs of bend segments of each tube might be established at 0.2 volts. Physical supports typically generate an eddy current voltage of 0.2 volts, so the baseline parameter for a physical support ROI might be established at 0.3 volts. Such baseline parameters typically will be based upon the various specifications of the steam generator and the nuclear power plant, along with theoretical and experimental data regarding the steam generator. It is understood, however, that the baseline parameters typically will be selected such that an eddy current sensor signal that exceeds a baseline parameter is worthy of further evaluation by an analyst, assuming that applicable exception data for the particular physical ROI does not already exist in the model. That is, the baseline parameters desirably will be selected such that no further action is triggered when the eddy current sensor signals are below that which should reasonably trigger further analysis of the particular physical ROI. It is understood, however, that various methodologies may be employed for establishing the baseline parameters of the exemplary ROIs without departing from the present concept.

It is also noted that the baseline parameters can include voltages, phase angles, pattern data, and any other type of characterization of an exemplary ROI that may be appropriate. The degree of sophistication of the baseline parameters is limited only by the ability to collect and analyze data regarding the tubes. As such, the baseline parameters of an exemplary ROI can be determined to be exceeded if any one or more of the various parameters in any combination are exceeded by a signal without limitation. Additionally or alternatively, the baseline parameters could have an even greater degree of sophistication wherein certain combinations of parameters need to be exceeded in a certain fashion for the system to trigger the need for further analysis, by way of example.

On the other hand, if it is determined, as at 216, that the signal for the physical ROI exceeds in some fashion the baseline parameters of the identified corresponding exemplary ROI, processing continues, as at 230, where it is determined whether exception data exists for the physical ROI that is under analysis. As mentioned elsewhere herein, the exception data advantageously will be a part of the model of the steam generator. If such exception data is determined at 230 to exist, processing continues, as at 234, where it is determined whether the signal from the physical ROI exceeds the exception data by a predetermined threshold. That is, it is not expected that the physical ROI that is the subject of the exception data will remain unchanged during the life of the steam generator, and rather it is expected that the physical ROI might degrade over time due to wear, corrosion, etc. Since the physical ROI has already been determined at the time of taking the historic data set to have a signal which exceeds the baseline parameters that would otherwise be expected from a similar ROI, the threshold that is already built into the baseline parameters is unlikely to be useful in evaluating the particular physical ROI that is the subject of the retrieved exception data. As such, a separate threshold is established based upon various factors which, if exceeded by the present signal from the physical ROI, will trigger further analysis as at 238, of this particular physical ROI. Such further analysis likely will be manual evaluation by an analyst. On the other hand, if it is determined at 234 that the signal from the physical ROI fails to exceed the retrieved exception data by the predetermined threshold, processing continues, as at 220, where no further action is taken for this particular physical ROI. Further evaluation by an analyst is also triggered, as at 238, if it is determined, as at 230, no exception data exists for this particular physical ROI.

It is noted that an additional notification can be triggered if the baseline parameters of the exemplary ROI are exceeded by a significant amount, or if the predetermined threshold for the exception data is exceeded by a significant amount, in order to alert an analyst that an increased level of attention should be directed to a particular physical ROI, for example. In the exemplary embodiment depicted herein, for instance, further analysis is triggered if either the baseline parameters of the exemplary ROI or the predetermined threshold of the exception data is exceeded in any fashion. However, an additional notification can be generated if the signal exceeds the baseline parameters or the predetermined threshold of the exception data by 25%, by way of example. It is understood that any type of criteria can be employed to trigger such heightened further analysis.

It therefore can be seen that the eddy current data that is collected from a tube under analysis is evaluated using the model that includes exemplary ROIs with baseline performance parameters and further includes exception data for ROIs of particular tubes, with the result being the triggering of further analysis such as evaluation by an analyst only in specific predefined circumstances such as would occur at 238. As such, the manual evaluation effort that is required of an analyst using the exemplary methods set forth herein is greatly reduced compared with known methodologies.

It is noted that the exemplary method depicted generally in FIG. 2 envisions a real-time automated analysis system wherein a signal that is collected from a tube is input directly into the location algorithm and is evaluated as it is collected. It is understood, however, that different methodologies may be employed. For instance, the data from one or more tubes can be collected and stored and then evaluated as a whole rather than being analyzed on a real-time basis. Other variations can be envisioned that are within the scope of the present concept.

Figure 3:
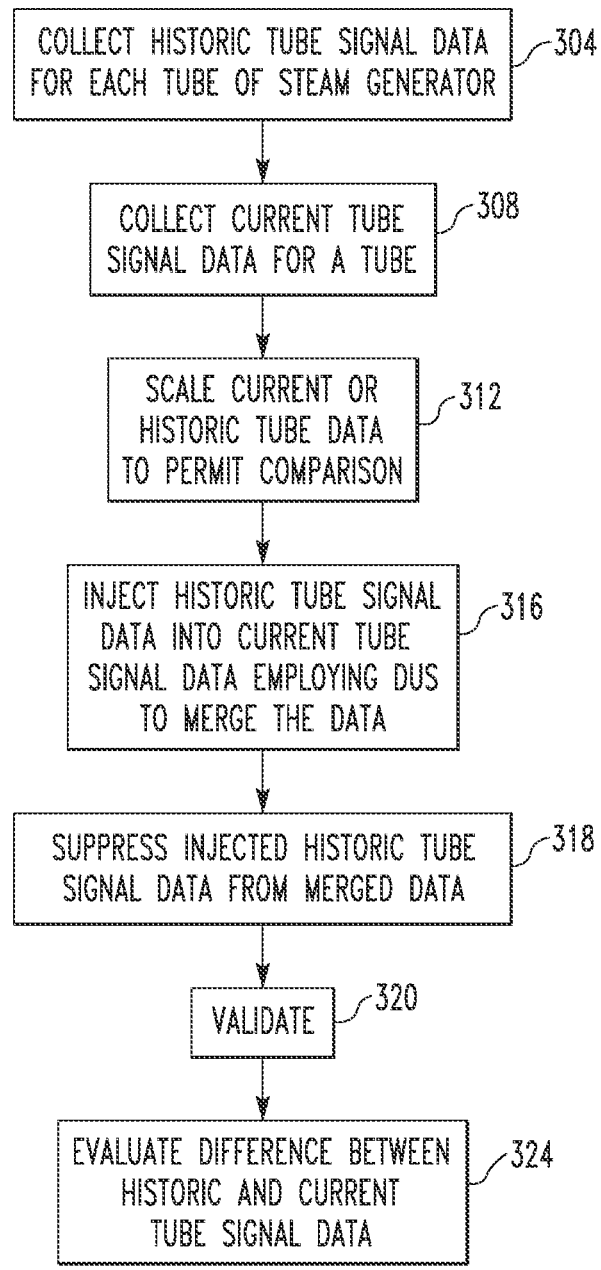

FIG. 3 generally depicts an exemplary methodology for analyzing signals of interest collected from regions or areas of interest of tubes in a steam generator that is undergoing analysis. As such, another aspect of the invention is to collect historic tube signal data for each tube, e.g., region or area of interest of a tube of a steam generator, as at 304, and employ the historic tube data for use at a later time in comparison with tubes, e.g., region or area of interest of a tube of a steam generator that is under analysis after a period of use. Advantageously, the historic data shares certain aspects with current collected data. The method advantageously merges the historical and current signal data, and suppresses from the current signal data any aspects that were also present in the historic tube data in order to generate an improved simpler signal that is indicative of a change in condition of the area or region of a tube under analysis. The historic tube signal data can be taken at the time of manufacture of the steam generator or can be taken at a later time, such as during an in-service inspection of a steam generator.

The historic tube signal data that is collected at 304 during manufacture or in-service inspection of a steam generator is then stored for future retrieval and comparison with subsequently collected data during a current testing operation. That is, current tube signal data is collected, as at 308, for a given tube of a steam generator. The historic tube data for the same tube is retrieved. It is typically the case that some type of scaling with respect to either the current data or the historic data will occur, as at 312, to permit comparison. By way of example, it may be necessary to reduce or increase or otherwise manipulate all of the values of either the current or historic data sets since different eddy current sensors or other instrumentation were employed to take both sets of data or because of other differing operating parameters between the eddy current sensors employed to take the historic and the current tube data. Other types of scaling may be necessary if the data points of the historic tube data do not match sufficiently with the data points of the current tube data. As mentioned elsewhere herein, data may be taken at thirty locations per inch, although forty-five locations per inch may likewise be employed, as can other data signal densities. Still other scaling may be required if the direction of movement of the eddy current sensor is different between the historic data and the current data. For example, the historic data may have been based upon longitudinal movement of an eddy current sensor in a direction from the tube sheet toward the tube sheet transition, whereas the current data may involve an eddy current sensor that is moving in a direction from the tube sheet transition toward the tube sheet. Regardless of the nature of the historic and current tube data, scaling or other mathematical manipulations may be performed at 312 to permit comparison between the two.

The historic tube signal data is then injected into the current tube signal data, as at 316. That is, these two data sets, i.e., the historic and the current tube data, are combined to form a merged tube signal data set. The merged data set is subjected to a suppression step. The injected historic tube data of the merged data set is suppressed, as at 318. The suppression process employs the ANSER ALFS (Axial Look Forward Suppression) software that is licensable from Westinghouse Electric Company, LLC, Cranberry Township, Pa. The ANSER software suppresses identified signals (e.g., tube sheet transition) and enhances degradation signal (e.g., ASME 20% flaw). Other suppression techniques and software may be used such as, but not limited to, simple mix. However, in certain embodiments wherein multiple year comparisons are to be performed, the ALFS is preferred because it has this capability. The suppression output is validated, as at 320. Validation provides verification of suppression of common mode signal not to exceed a predetermined voltage (such as 0.5 V) and enhancement does not distort the sample defect as well as preserves its phase and voltage (e.g., 20% hole signal at greater than 4V and more than 140 degrees) and thus, increases confidence in the ability of the process to accurately detect degradation. As a result, a new signal is generated which is representative of the change in condition of the tube, e.g., area/signal of interest, that is under analysis between the time at which the historic tube data was collected, such as at the time of manufacture or during an in-service inspection, and the time at which the current tube data is collected.

The injection and suppression of the tube data, as at 316 and 318, can be performed by employing suitable software, such as but not limited to Data Union Software (DUS) which is licensable from Westinghouse Electric Corporation, LLC, Cranberry Township, Pa. The DUS software generally provides for combining, e.g., merging, mixing or injecting, two data sets, e.g., historic and current tube signal data, to produce a data set that is a combination of the two data sets. Employing DUS provides advantages over prior art software, such as but not limited to, the ability to: (i) process historical and current data sets that may be collected using different instruments and operating parameters; (ii) subject both the historic and current data sets to a common mode data noise environment in order to suppress any common mode signal; (iii) perform suppression on merged data to increase the speed and efficiency of the process, and (iv) apply in a cumulative manner to permit multiple sets of historic data to be compared with current data with efficiency and high accuracy.

Figure 4:
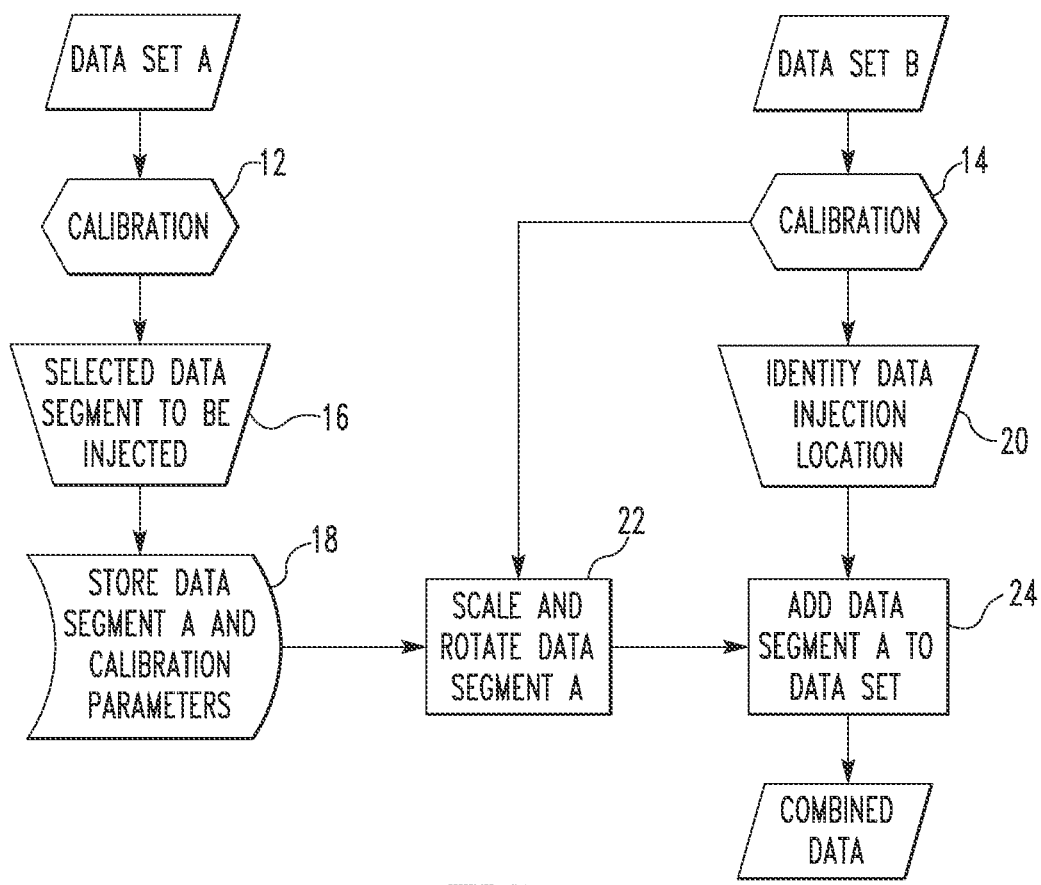

A flow chart of an overall data combination process for use in this invention is shown in FIG. 4. Referring to FIG. 4, the first steps 12 and 14 in the data injection process are to define the calibration or normalization parameters for each Data Set A and B, wherein A represents historic tube sheet transition data and B represents current tube sheet transition data. Preferably, at least one of the standard holes or notches in a calibration standard used for this purpose should be identical for both data sets. If they are not identical, mathematical models can be used as a basis for interpolation of one or the other of the data sets. The calibration standard is a specimen created in accordance with the ASME code. Each of the data sets is then calibrated so that the reference discontinuity response for the two data sets, A and B, is identical. For most applications, it can be assumed that the accuracy of the standard is sufficient so that cross calibration of the standards is not required.

After the calibration parameters are established, the segment of data from data set A to be inserted into data set B is selected and stored in step 16, shown in FIG. 4. In the DUS system, this is accomplished by superposition of the calibration signal into a duplicate segment of current data. This data then can be used for enhancement of historic comparison, as well as validation to ensure the result of comparison has not distorted the injected calibration signal. The data segment A along with the calibration parameters for that segment determined in step 12 is then stored in a file. Multiple segments from the same tube or specimen can be stored and each identified with a ROW/Col. and sequence number as represented by step 18 in FIG. 4.

Referring to FIG. 4, after the segments of interest have been identified, the data set B in which the segment is to be inserted is read into the machine. The location where the segment is to be inserted is chosen in step 20. In the DUS system, this is accomplished by duplicating a segment of current data in the free span that is free of structure signal or other anomalies. Once the segment A data is selected, the appropriate calculations are made in step 22, based upon the calibration parameters, to rotate and scale the segment A data so that it has the same calibration factors as data set B. The thus normalized segment A data is then added to the displayed data set in step 24 shown in FIG. 4. To display the results with the DUS system, data set B must be reread into the machine. This process can be repeated with different sets of data from different years thus, permitting historical comparison of multiple years.

In the foregoing embodiment, the segment A data is added into the displayed data. If desired, the segment A data could equally well replace some of the displayed data in set B. Furthermore, since the data set that is being displayed is the file that is modified, it is important that the combination process take place on a copy of the data and not the original file. Once the combination process is complete, the new data set can be manipulated in the same way as any other data set. No knowledge of the data combination process is retained in the combined file.

In certain embodiments, it may be desirable to amplify one or more portions of the new signal that is generated. Such an amplified signal would emphasize those aspects of the new signal that would be even more indicative of a change in the condition of the tube sheet transition between the time the historic data was collected and the time that the current data is collected.

The signal is then submitted, as at 324, for evaluation. Such evaluation may be performed automatically or may be performed manually by an analyst. It is then determined whether any additional tubes of the steam generator require analysis with respect to their tube region. If further tubes require analysis, processing continues. Otherwise, processing ends.

In this regard, it is understood that the aforementioned tube analysis can be performed as a part of the analysis depicted generally in FIG. 2 or can be performed separately. In this regard, the historic tube data that was collected at 304 potentially can be saved as part of the model of the steam generator, particularly as a special part of the exception data set. As such, it may be possible to completely analyze a tube from one tube sheet transition through its longitudinal extent and to its opposite tube sheet transition using the teachings herein. As mentioned elsewhere herein, however, it is possible to analyze the tube sheet transitions separately from the other portions of the tubes, as may be desired.

As previously mentioned, the analysis methodology depicted in FIG. 3 is applicable to signals of interest collected from regions or areas of interest of the tubes of a steam generator. Thus, the methodology can be used throughout the steam generator tube to analyze dents, supports, straight length segments, tube sheets, transitions, and the like. In certain embodiments, the methodology is useful in analyzing tube sheet transition regions. Due to the thickness of the tube sheet, the eddy current data that is collected from a tube in the tube sheet transition region typically is of a voltage far in excess of any of the baseline parameters of any of the exemplary ROIs. Moreover, the variation in eddy current voltage from one tube sheet transition to another is also far in excess of any baseline parameter of an exemplary ROI. For instance, and has been mentioned elsewhere herein, the eddy current voltage for a tube sheet transition might be on the order of thirty (30.0) volts. The eddy current voltage of another tube sheet transition might be 25.0 volts, and that of another tube might be 35.0 volts. Since the eddy current voltages at tube sheet transitions are one or more orders of magnitude greater than any voltage that would be generated in other portions of the tube, i.e., portions other than the tube sheet transition, the method depicted in FIG. 3 is useful to facilitate the analysis of signals collected from tube sheet transitions of a steam generator that is undergoing analysis. In general terms, it is understood that the eddy current signals from tubes in the tube sheet transition area of a steam generator are of a voltage that is sufficiently high that the portion of the eddy current signal which might indicate a possible flaw, i.e., the signal of interest, which might be on the order of 0.1 volts, is far too small in comparison with the overall eddy current signal to be easily detected or evaluated.

It is also noted that the teachings employed herein can be applied in a cumulative fashion to permit multiple sets of historic data to be compared with current data. That is, historic data can be taken at a first time, such as at the time of manufacture of a steam generator or at an in-service inspection, and such historic data can be employed during a subsequent evaluation of the steam generator tubes. The data that is developed during such a subsequent evaluation may then be stored as a second historic data set. Both historic data sets can then be compared with data that is collected during a further inspection of the steam generator to enable the change in the condition of various tubes to be charted as a function of time over the course of several inspections that occur at several different times. Other uses of the data can be envisioned.

It is understood that the analysis described herein can be performed on a digital computer or other processor of a type that is generally known. For instance, such a computer might include a processor and a memory, with the memory having stored therein one or more routines which can be executed on the processor. The memory can be any of a wide variety of machine readable storage media such as RAM, ROM, EPROM, EEPROM, FLASH, and the like without limitation. The signal from the eddy current sensor might be received by an analog-to-digital converter which provides a digital input to the computer for processing and storage of the signals. The historic and current data can be stored on any such storage media and can potentially be transported or transmitted for use on other computers or processors as needed.

According to the invention, the TITAN process provides advantages over known processes, as well as advantages over each of the separate, individual EADS and RTAA processes. Such advantages can include at least one of the following:

(i) EADS is a rule-based vector extraction algorithm that has been used in the industry for over 20 years;

(ii) RTAA is a noise-based signal extraction algorithm that has been used in the industry for the at least several years;

(iii) Both EADS and RTAA complement each other and provide effective primary and secondary analysis in compliance with current industry guidelines;

(iv) Both EADS and RTAA has proven records to be effective analysis processes for all type of steam generator inspection tubing;

(v) A single combined analysis report from two methods to produce the final results of steam generator tubing inspection for ease of review;

(vi) Ability for the user to identify which of the automated analysis methods is providing the tube condition report entry; and (vii) An integrated noise evaluation process.

In accordance with the invention, the output is a single resolved report between EADS and RTAA that can be reviewed by fewer and less experienced analysts to improve human performance. The TITAN system and its output provide a comprehensive illustration of steam generator tube conditions. This process and the final report can be used to determine proper action in steam generator tubing maintenance. The integrated systems and methods of the invention provide defense in depth and multiple barrier of defense, as follows:

(i) Dual Setup method (automated by system and semi-automated by noise analysts);

(ii) Dual Located algorithm (adaptive threshold and pattern recognition);

(iii) Landmark validation that verifies locate algorithm correctness;

(iv) Gap verification from noise measurements to ensure system performance is as expected and complete analysis of data of interest;

(v) Integrate Report Analysis Tool to verify that must detect signals are identified by both methods;

(vi) Enhanced graphical Automated Analysis Analyzer; and (vii) Integrate Automated Compare and resolution process to identify common and different reportable entries of tube conditions by two automated analysis processes.

Figure 5:
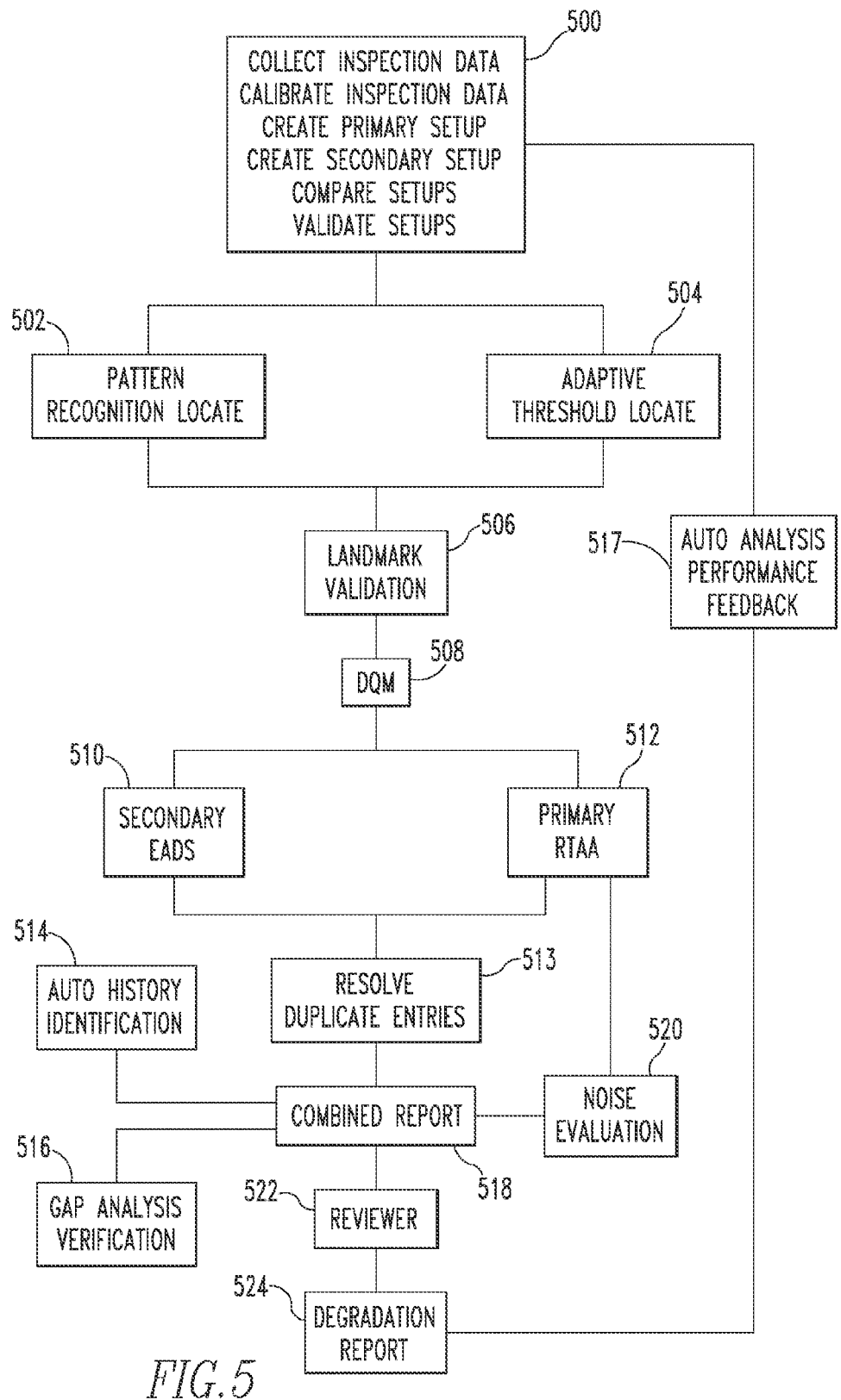
FIG. 5 is a flow chart depicting certain aspects of the invention.

FIG. 5 is a schematic showing a steam generator inspection and automated analysis process in accordance with certain embodiments of the invention. In system setup 500, inspection data is collected, the data is automatically or manually calibrated, an automated primary setup and semi-automated secondary setup is created, and the primary and secondary setups are compared and validated. In certain embodiments, the data is automatically calibrated as it is collected. Calibration software that automatically recognizes the calibration standard signals can be employed. The software performs calibration and creates an automated primary setup. Alternatively, a person can perform the calibration manually and then create a secondary setup. The primary and secondary setups are typically compared against each other and validated against a setup history to ensure correctness of the information. Dual independent setup processes provide a barrier of defense to ensure that the system is properly calibrated. The steps conducted in system setup 500 can include the setup steps previously disclosed herein.

As shown in FIG. 5, the data generated in system setup 500 is then passed through a dual locating algorithm process that includes a pattern recognition locating algorithm 502 and an adaptive threshold locating algorithm 504. The results from both algorithms 502,504 are validated against each other in a landmark validation 506 to ensure accurate and reliable results. Algorithms 502,504 are employed to identify tube support structure signals along tube data, and the tube support structure allows data segmentation for analysis. Dual locating algorithms can provide additional barriers of defense to ensure that data segments are located properly for further analysis.

Upon successful validation, data is processed through a data quality monitoring (DQM) module 508 to ensure that the data passes certain strict quality guidelines established by EPRI. The module 508 measures and detects data quality issues such as excessive noise spike, sampling density, and the like. If the data quality is not accepted, the information is logged as a quality problem and an operator an alerted accordingly.

Once the module data is accepted in module 508, the data is analyzed by secondary EADS 510 and primary RTAA 512. The steps conducted in the secondary EADS 510 and primary RTAA 512 can include the analysis steps previously disclosed herein.

Each of the EADS 510 and RTAA 512 processes produces analysis reports, which are automatically resolved in block 513. The resolving of the analysis report includes (i) identifying common and duplicate entries from each primary and secondary report, and selecting a single entry for a resolution report 518; and (ii) identifying entries that are reported by one automated method but not by the other, and entering such entries into the single resolution report 518. In accordance with the invention, TITAN can determine duplicate report entries by checking the difference, or discrepancy, between report entry data points. If the difference between the data points is less than a user defined tolerance, the data points are considered to be duplicates. Duplicate entries are then passed through a user defined resolving logic to determine which one of the report entries should be retained and entered into the single resolution report. The default convention is conservative by retaining and reporting the most severe of the two common report entries. For example, entries with possible tube degradation, such as, cracking, will be retained if found to be duplicates with other entries, which indicate a tube anomaly, such as, dent. If duplicate entries are of the same type, the entry with a larger signal amplitude will be the one entry that is retained.

An auto-history identification 514 process is then implemented to compare current resolved outputs with previous inspection results. If there are results from a previous inspection that are not identified with the current process, further analysis will be performed on the current data to create a report with entries that match previous inspection results.

As shown in FIG. 5, a noise evaluation module 520 performs a check to ensure that all unusual noise signals are evaluated and entered into the report, which serves as an additional barrier of defense to ensure that unforeseen conditions and unusual data are being noted for further evaluation.

In accordance with the invention, a noise measurement from RTAA may also be tabulated to ensure complete noise measurement of all data of interest. This process ensures complete analysis coverage of the RTAA process and results in a report that identifies any gap in measurement or analysis. As shown in FIG. 5, a gap analysis verification 516 generates results in a report to identify any gap in measurement or analysis.

Also, an automatic analysis performance feedback 517 is provided to ensure that each EADS and RTAA method performs as expected. The feedback report ensures that all of the important and critical signals are identified by both methods.

The data generated in the single resolved report 518 is then reviewed and resolved by a reviewer 522. Any tube degradation identified in the single report 518 is confirmed by the reviewer 522 and a degradation report 224 is created.

In general, the systems and methods of the invention can be used to generate data and a single report for analysis to determine proper action in steam generator tubing maintenance. Also, the invention meets the current industry guidelines by implementing two independent automated algorithms, each of which are qualified independently by EPRI. The use of any other similar system would require the users deviate from industry guidelines and notify the NRC before usage. Furthermore, the invention maximizes effectiveness by combining accuracy and consistency of an automated system and expert knowledge of experienced workers resulting in accurate and reliable output. Moreover, the invention combines automated and semi-manual methods of setup and verification to increase barrier of defense in depth. Finally, the invention integrates monitoring, feedback and validation phases during operation to detect unusual conditions that may impact system performance.

It should be appreciated by those skilled in the art that this invention is not limited to this particular application and/or embodiment. Other applications are contemplated as being within the scope of the invention.

Accordingly, the particular embodiments disclosed are meant to be illustrative only and not limiting as to the scope of the invention which is to be given the full breadth of the appended claims and any and all equivalents thereof.

What is claimed is:

1. A method of non-destructively assessing a current condition of a number of tubes of a steam generator of a nuclear power plant, the method comprising:

(a) establishing a model of the steam generator that comprises a set of baseline parameters for each of a plurality of exemplary regions of interest (ROIs) of a number of the tubes of the steam generator;

(b) extracting a signal from each of a number of physical ROIs of a number the tubes;

(c) comparing the signal from a given physical ROI of a tube with the set of baseline parameters of the corresponding exemplary ROI of the model;

(d) triggering additional processing when at least a portion of the signal from the given physical ROI exceeds at least a portion of the set of baseline parameters of the corresponding exemplary ROI;

(e) employing a primary automated analysis code for conducting steps (a) through (d);

(f) generating a first set of results based on the primary automated analysis code;

(g) employing a different secondary automated analysis code for conducting steps (a) through (d);

(h) generating a second set of results based on the different secondary automated analysis code;

(i) combining the first set of results and the second set of results; and (j) producing a single report including output from each of the first set of results and the second set of results generated by the primary automated analysis code and the different secondary automated analysis code, respectively, absent of duplicate entries.

2. The method of claim 1, wherein the combining of the first and second sets of results in step (i) comprises, automatically comparing the first and second sets of results, identifying a common and duplicate entry generated by the primary automated analysis code and the different secondary automated analysis code, and selecting a single entry as output in the single report.

3. The method of claim 1, wherein the combining of the first and second sets of results in step (i) comprises automatically comparing the first and second sets of results, identifying any entry that is reported by only one of the primary automated analysis code and the different secondary automated analysis code, and providing the entry as output in the single report.

4. The method of claim 1, wherein prior to step (e), the method further comprises:
generating pattern recognition data;
generating adaptive threshold data; and
validating the pattern recognition and threshold data against each other.

5. The method of claim 1, further comprising comparing the output in the single report with previous inspection results.

6. The method of claim 1, further comprising verifying any gap in measurement or analysis.

7. The method of claim 1, further comprising performing a check ensuring that all unusual noise signals are evaluated and entered into the single report.

8. The method of claim 1, wherein one of the secondary and primary automated analysis codes is EADS and the other is RTAA.

9. The method of claim 1, further comprising refraining from the triggering of additional processing with respect to a particular physical ROI when no portion of a signal from the particular physical ROI exceeds a set of baseline parameters of a corresponding exemplary ROI.

10. The method of claim 1, further comprising triggering an additional notification if the at least portion of the signal from the given physical ROI exceeds the at least portion of the set of baseline parameters of the corresponding exemplary ROI by a predetermined amount.

11. The method of claim 1, wherein the model further comprises an exception data set for each of one or more physical ROIs of each of one or more tubes of the number of tubes, each exception data set being representative of a preexisting signal of the physical ROI that exceeds the set of baseline parameters of the corresponding exemplary ROI, and wherein the triggering of additional processing comprises seeking in the model an exception data set for the given physical ROI.

* * * * *